United States Patent
Lim et al.

(10) Patent No.: US 12,268,528 B2
(45) Date of Patent: Apr. 8, 2025

(54) SYSTEM AND METHOD FOR ANALYZING CORNEAL LESION USING ANTERIOR OCULAR SEGMENT IMAGE, AND COMPUTER-READABLE RECORDING MEDIUM

(71) Applicant: SAMSUNG LIFE PUBLIC WELFARE FOUNDATION, Seoul (KR)

(72) Inventors: Dong Hui Lim, Seoul (KR); Gyu Le Han, Seoul (KR); Young Jun Kim, Busan (KR); Yong Man Ro, Daejeon (KR); Hye Bin Lee, Daejeon (KR)

(73) Assignee: SAMSUNG LIFE PUBLIC WELFARE FOUNDATION (KR)

( * ) Notice: Subject to any disclaimer, the term of this patent is extended or adjusted under 35 U.S.C. 154(b) by 560 days.

(21) Appl. No.: 17/784,140

(22) PCT Filed: Dec. 10, 2020

(86) PCT No.: PCT/KR2020/018049
§ 371 (c)(1),
(2) Date: Jul. 29, 2022

(87) PCT Pub. No.: WO2021/118255
PCT Pub. Date: Jun. 17, 2021

(65) Prior Publication Data
US 2023/0022921 A1    Jan. 26, 2023

(30) Foreign Application Priority Data
Dec. 10, 2019    (KR) ........................ 10-2019-0164182

(51) Int. Cl.
*A61B 3/117*    (2006.01)
*A61B 3/00*    (2006.01)
(Continued)

(52) U.S. Cl.
CPC .......... *A61B 5/7264* (2013.01); *A61B 3/0025* (2013.01); *A61B 3/117* (2013.01);
(Continued)

(58) Field of Classification Search
CPC ..... A61B 5/7264; A61B 3/0025; A61B 3/117; A61B 2576/02; A61B 5/0077; A61B 3/14;
(Continued)

(56) References Cited

U.S. PATENT DOCUMENTS 10,468,142 B1 * 11/2019 Abou Shousha ...... G16H 30/20
11,704,791 B2 * 7/2023 Yang ..................... G06T 7/0012
(Continued)

FOREIGN PATENT DOCUMENTS

KR    10-1848321 B1    4/2018
KR    10-2019-0022216 A    6/2019
(Continued)

OTHER PUBLICATIONS

International Search Report in related PCT/KR2020/018049, dated Jun. 8, 2021, 4 pages.
(Continued)

*Primary Examiner* — Cindy Trandai
(74) *Attorney, Agent, or Firm* — Dilworth IP, LLC (57) ABSTRACT

A system for and a method of analyzing a corneal lesion using an anterior segment image according to the present invention. The system includes: an image acquisition unit configured to acquire an anterior segment image from the eyeball of a subject, a feature extractor configured to extract feature information on a position and a cause of a lesion in the cornea from the anterior segment image by applying a convolution layer to the anterior segment image through machine learning on the basis of a database in which clinical information pre-acquired by analyzing positions and causes (Continued)

of lesions in the corneas of subjects is stored; and a result determination unit configured to identify a position of the cornea from the anterior segment image using the feature information and to analyze and determine the position and the cause of the lesion in the cornea from the position of the cornea.

10 Claims, 7 Drawing Sheets

(51) Int. Cl.
*A61B 5/00* (2006.01)
*G06T 7/00* (2017.01)
*G06T 7/73* (2017.01)
*G06V 10/44* (2022.01)

(52) U.S. Cl.
CPC .............. *G06T 7/0012* (2013.01); *G06T 7/73* (2017.01); *G06V 10/44* (2022.01); *G06T 2207/20084* (2013.01); *G06T 2207/30041* (2013.01); *G06T 2207/30096* (2013.01)

(58) Field of Classification Search
CPC ....... A61B 3/0008; G06T 7/0012; G06T 7/73; G06T 2207/20084; G06T 2207/30041; G06T 2207/30096; G06T 2207/20088; G06T 2207/20081; G06V 10/44; G06V 2201/03; G06V 10/82; G06N 3/04; G06N 3/08; G06N 20/00; G06N 3/042; G16H 50/20

See application file for complete search history.

(56) References Cited

U.S. PATENT DOCUMENTS

| | | | |
|---|---|---|---|
| 11,887,303 B2 * | 1/2024 | Shi | G06V 10/82 |
| 2016/0183796 A1 * | 6/2016 | Fukuma | A61B 5/1171 |
| | | | 351/200 |
| 2018/0174031 A1 | 6/2018 | Yang et al. | |
| 2019/0105200 A1 * | 4/2019 | Hipsley | A61F 9/00825 |
| 2019/0269326 A1 * | 9/2019 | McWherter | A61B 3/0008 |
| 2020/0288972 A1 | 9/2020 | Park et al. | |
| 2020/0405147 A1 * | 12/2020 | Nagarajan | A61B 3/158 |
| 2021/0267451 A1 * | 9/2021 | Durr | A61B 5/6898 |
| 2022/0044403 A1 * | 2/2022 | Ayatsuka | A61B 3/152 |
| 2022/0257115 A1 * | 8/2022 | Razali | G16H 30/20 |
| 2023/0130244 A1 * | 4/2023 | Hirokawa | A61B 5/02007 |
| | | | 382/128 |
| 2023/0301511 A1 * | 9/2023 | Tsukada | A61B 3/10 |

FOREIGN PATENT DOCUMENTS

| | | |
|---|---|---|
| KR | 10-2019-0074477 A | 6/2019 |
| KR | 1020190087272 A | 7/2019 |

OTHER PUBLICATIONS

Written Opinion in related PCT/KR2020/018049, dated Jun. 18, 2021, 5 pages.

* cited by examiner

SYSTEM AND METHOD FOR ANALYZING CORNEAL LESION USING ANTERIOR OCULAR SEGMENT IMAGE, AND COMPUTER-READABLE RECORDING MEDIUM

TECHNICAL FIELD

The present invention relates to a system for and a method of analyzing a corneal lesion using an anterior segment image and, particularly, to a system for and a method of analyzing a position and a cause of an ocular disease in an anterior segment image by performing machine learning of clinical information of a subject on the basis of deep learning.

BACKGROUND ART

The cornea is the outermost surface of the eyeball and is the colorless transparent outer covering at the front of the eyeball. The cornea is composed of five layers: epithelium, Bowman's membrane, stroma, Descemet's membrane, and endothelium in order from the outermost surface inward. Stroma is composed of flat fibroblasts and a collagen fiber having an arrangement of regular layers in the shape of a plate.

The cornea is the part of the eye through which light first passes, and blood vessels are not distributed in the cornea. In addition, the corneal surface is kept wetted with tears. The tears serve to constantly transmit and refract light, and thus an ordinary person can maintain 20/20 vision or better.

The cornea covers the front portion of the eye, and thus may be subject to damage due to trauma, infection, and other immune reactions. As a result, the cornea may lose properties of the transparent cornea, leading to corneal opacity, or a new blood vessel may be formed, leading to serious vision loss. Keratitis is a disease that causes inflammation of the cornea that results from an infection or a non-infection. When not treated properly, keratitis causes damage to corneal tissue and increases the risk of decreased vision due to the occurrence of corneal opacity.

Particularly, because developing keratitis may cause permanent vision loss, an earlier diagnosis and treatment thereof are very important. Keratitis causes hyperemia, a feeling of being in contact with a foreign substance, and a pain. Symptoms of keratitis are sensitiveness to light, excessive tears, and blurred vision. Keratitis may be associated with an infection or a non-infection. Examples of non-infectious keratitis include aseptic keratitis due to a corneal immune reaction, toxic keratitis due to a drug, neurotrophic keratitis due to damage to a corneal nerve, and the like. Infectious keratitis is caused by infection of the cornea with various of pathogens, such as bacteria, viruses, and fungi. Bacteria causing infectious keratitis include staphylococcus or streptococcus that is gram-positive and pseudomonsa aeruginosa that is gram-negative. Viruses causing infectious keratitis include herpes simplex virus. Fungi causing infectious keratitis include fusarium and candida.

More than 2.3 million people per year in Korea receive a hospital treatment for keratitis, and the total amount of medical expenses incurred as of 2018 amounted to more than KRW 110 billion. In addition, with an increase in the use of contact lenses, an incidence rate of keratitis is expected to continuously increase. However, a diagnosis with keratitis depends entirely on the knowledge and experience of ophthalmologists.

An ophthalmologist makes a diagnosis by directly observing an anterior segment of eye using a slit lamp microscope or cultivates a corneal specimen for identifying a cause of keratitis.

The golden standard is the cultivation of the corneal specimen. However, it takes a long time to cultivate the corneal specimen, with the result that a cultivation rate is low. In an actual clinical practice, a treatment for keratitis cannot be delayed until a result of the specimen cultivation is available. Therefore, the ophthalmologist first provides an empirical treatment based on the result of identifying a shape, size, interface, position, and the like of a lesion using the slit lamp microscope. Then, a treatment based on the result of the cultivation specimen is provided instead of the previous treatment method.

However, infectious keratitis caused by bacteria, fungi, amoebas, and viruses and non-infectious keratitis are not clearly distinguished from each other in a clinical manner. Due to an erroneous diagnosis, an unnecessary treatment may be provided for a long time or a required treatment may not be provided at an appropriate time. In this case, without suffering from decreased vision, a patient may have vision that would have been improved if an accurate diagnosis and a quick treatment were provided at an appropriate time. Moreover, there occurs a problem in that the patient's quality of life may be decreased and that the amount of medical expenses may be increased.

SUMMARY OF THE INVENTION

Technical Problem

An object of the present invention, which is made to solve the problem as mentioned above, is to provide a system for analyzing a corneal lesion using an anterior segment image in such a manner that an accurate quick diagnosis is provided through machine learning.

Another object of the present invention is to provide a method of analyzing a corneal lesion using an anterior segment image in order to increase the accuracy of a diagnosis in a process of applying machine learning.

Still another object of the present invention is to provide a computer-readable storage device on which to store a program that performs a method of analyzing a corneal lesion that is realized using the above-mentioned system.

Technical Solution

In order to accomplish the above-mentioned objects, according to an aspect of the present invention, there is provided a system for analyzing a corneal lesion using an anterior segment image, the system including: an image acquisition unit configured to acquire an anterior segment image from the eyeball of a subject; a feature extractor configured to extract feature information on a position and a cause of a lesion in the cornea from the anterior segment image by applying a convolution layer to the anterior segment image through machine learning on the basis of a database in which clinical information pre-acquired by analyzing positions and causes of lesions in the corneas of subjects is stored; and a result determination unit configured to identify a position of the cornea from the anterior segment image using the feature information and to analyze and determine the position and the cause of the lesion in the cornea from the position of the cornea.

In the system, the feature extractor may include a residual network (ResNet) obtained by stacking at least one network of a plurality of networks each including a convolution layer, a pooling layer, and an activation function or a rectified linear unit (ReLU) function and the ResNet may extract the feature information, including a multiple-channel feature map for extracting a suspicious region, from the anterior segment image.

In the system, the feature extractor may include a lesion guiding module configured to extract a lesion region more precise than the suspicious region through convolution of the feature information and positional data of a lesion in the clinical information, the positional data representing a position of the lesion.

In the system, the feature extractor may include a slit lamp mask adjustment module configured to adjust a slit beam image present in a region of the anterior segment image.

In the system, the slit lamp mask adjustment module may exclude a slit lamp portion from the anterior segment image and may cause the position of the cornea or the position of the lesion in the cornea, which is included in the anterior segment image, to be learned.

In the system, the slit lamp mask adjustment module may apply the convolution layer to a $3^{rd}$ label feature vector of the anterior segment image and then may adjust a masking ratio by applying a weighting factor for a slit beam portion.

In the system, the result determination unit may re-input a $3^{rd}$ label feature vector output from the feature extractor and a prediction vector corresponding to a $2^{nd}$ label feature vector computed by applying a fully connected layer to the $3^{rd}$ label feature vector, into the fully connected layer and thus may identify the cause of the lesion in the cornea.

According to a second aspect of the present invention, there is provided a method of analyzing a corneal lesion using an anterior segment image, the method of processing steps realized by constituent elements of a system for analyzing a corneal lesion, the method including: a step of acquiring, by an image acquisition unit, an anterior segment image from the eyeball of a subject; a step of extracting, by a feature extractor, feature information on a position and a cause of a lesion in the cornea from the anterior segment image by applying a convolution layer to the anterior segment image and a database in which clinical information pre-acquired by analyzing positions and causes of lesions in the corneas of subjects is stored; and a step of analyzing and determining, by a result determination unit, the position and the cause of the lesion in the cornea after identifying a position of the cornea from the anterior segment image using the feature information.

In the method, the step of extracting, by the feature extractor, the feature information may include a step of extracting the feature information including a multiple-channel feature map for extracting a suspicious region, from the anterior segment image, the feature information being destined for a residual network (ResNet) obtained by stacking at least one network of a plurality of networks each including a convolution layer, a pooling layer, and an activation function or a rectified linear unit (ReLU) function.

In the method, the step of extracting the feature information may include a step of extracting a lesion region more precise than the suspicious region through convolution of the feature information and positional data of a lesion in the clinical information, the positional data representing a position of the lesion, by a lesion guiding module (LGM).

In the method, the step of extracting, by the feature extractor, the feature information may include a step of adjusting, by a slit lamp mask adjustment module (MAM) of the feature extractor, a slit beam image present in a region of the anterior segment image.

In the method, the step of adjusting, by the slit lamp mask adjustment module, the slit beam image may include a step of applying, the slit lamp mask adjustment module, the convolution layer to the anterior segment image and an already-collected slit lamp region mask; and a step of adjusting a masking ratio by applying a weighting factor for a slit beam portion.

In the method, the step of analyzing and determining, by the result determination unit, the position and the cause of the lesion in the cornea may include: a step of outputting, by the feature extractor, a 3rd label feature vector; a step of outputting a prediction vector corresponding to a $2^{nd}$ label feature vector computed by applying a fully connected layer to the 3rd label feature vector; and a step of re-inputting, by the result determination unit, the feature vector and the prediction vector to the fully connected layer.

According to still another aspect of the present invention, there is provided a computer-readable storage device on which a program that performs the method of analyzing a corneal lesion is recorded.

Advantageous Effects

The system for and the method of analyzing a corneal lesion according to the present invention, which are configured as described above, can provide the advantageous effect of lowering a misdiagnosis rate through an accurate quick diagnosis using a diagnosis model that results from learning on the basis of clinical information.

The system and the method according to the present invention can provide the advantageous effect of making a suitable diagnosis consistent with a current trend on the basis of a database continually updated because susceptibility of a causative organism to an antibiotic tends to change with time.

The system and the method according to the present invention can be utilized when an ophthalmologist makes a diagnosis as keratitis, and thus can provide the advantageous effect of possibly improving access to medical services in an area where a few licensed medical facilities are located and where the ophthalmologist does not do his/her medical practice or access of those living in poverty to the medical services.

DETAILED DESCRIPTION OF THE INVENTION

Best Mode

In order to accomplish the above-mentioned objects, according to an aspect of the present invention, there is provided a system for analyzing a corneal lesion using an anterior segment image, the system including: an image acquisition unit configured to acquire an anterior segment image from the eyeball of a subject; a feature extractor configured to extract feature information on a position and a cause of a lesion in the cornea from the anterior segment image by applying a convolution layer to the anterior segment image through machine learning on the basis of a database in which clinical information pre-acquired by analyzing positions and causes of lesions in the corneas of subjects is stored; and a result determination unit configured to identify a position of the cornea from the anterior segment image using the feature information and to analyze and determine the position and the cause of the lesion in the cornea from the position of the cornea.

In the system, the feature extractor may include a residual network (ResNet) obtained by stacking at least one network of a plurality of networks each including a convolution layer, a pooling layer, and an activation function or a rectified linear unit (ReLU) function and the ResNet may extract the feature information, including a multiple-channel feature map for extracting a suspicious region, from the anterior segment image.

In the system, the feature extractor may include a lesion guiding module configured to extract a lesion region more precise than the suspicious region through convolution of the feature information and positional data of a lesion in the clinical information, the positional data representing a position of the lesion.

In the system, the feature extractor may include a slit lamp mask adjustment module configured adjust a slit beam image present in a region of the anterior segment image.

In the system, the slit lamp mask adjustment module may exclude a slit lamp portion from the anterior segment image and may cause the position of the cornea or the position of the lesion in the cornea, which is included in the anterior segment image, to be learned.

In the system, the slit lamp mask adjustment module may apply the convolution layer to a $3^{rd}$ label feature vector of the anterior segment image and then may adjust a masking ratio by applying a weighting factor for a slit beam portion.

In the system, the result determination unit may re-input a $3^{rd}$ label feature vector output from the feature extractor and a prediction vector corresponding to a $2^{nd}$ label feature vector computed by applying a fully connected layer to the $3^{rd}$ label feature vector, into the fully connected layer and thus may identify the cause of the lesion in the cornea.

According to another aspect of the present invention, there is provided a method of analyzing a corneal lesion using an anterior segment image, the method of processing steps realized by constituent elements of a system for analyzing a corneal lesion, the method including: a step of acquiring, by an image acquisition unit, an anterior segment image from the eyeball of a subject; a step of extracting, by a feature extractor, feature information on a position and a cause of a lesion in the cornea from the anterior segment image by applying a convolution layer to the anterior segment image and a database in which clinical information pre-acquired by analyzing positions and causes of lesions in the corneas of subjects is stored; and a step of analyzing and determining, by a result determination unit, the position and the cause of the lesion in the cornea after identifying a position of the cornea from the anterior segment image using the feature information.

In the method, in the step of extracting, by the feature extractor, the feature information may include a step of extracting the feature information including a multiple-channel feature map for extracting a suspicious region, from the anterior segment image, the feature information being destined for a residual network (ResNet) obtained by stacking at least one network of a plurality of networks each including a convolution layer, a pooling layer, and an activation function or a rectified linear unit (ReLU) function.

In the method, the step of extracting the feature information may include a step of extracting a lesion region more precise than the suspicious region through convolution of the feature information and positional data of a lesion in the clinical information, the positional data representing a position of the lesion, by a lesion attention module.

In the method, the step of extracting, by the feature extractor, the feature information may include a step of adjusting, by a slit lamp mask adjustment module of the feature extractor, a slit beam image present in a region of the anterior segment image.

In the method, the step of adjusting, by the slit lamp mask adjustment module, the slit beam image may include a step of applying, the slit lamp mask adjustment module, the convolution layer to the anterior segment image and an already-collected slit lamp region mask; and a step of adjusting a masking ratio by applying a weighting factor for a slit beam portion.

In the method, the step of analyzing and determining, by the result determination unit, the position and the cause of the lesion in the cornea may include: a step of outputting, by the feature extractor, a $3^{rd}$ label feature vector; a step of outputting a prediction vector corresponding to a $2^{nd}$ label feature vector computed by applying a fully connected layer to the $3^{rd}$ label feature vector; and a step of re-inputting, by the result determination unit, the feature vector and the prediction vector to the fully connected layer.

According to still another aspect of the present invention, there is provided a computer-readable storage device on which a program that performs the method of analyzing a corneal lesion is recorded.

Mode for Invention

The terms to be used throughout the present specification are briefly described, and the present invention is in detail described.

The terms to be used throughout the present specification are selected from among general terms that are currently used as widely as possible, considering a functional meaning in the present specification. However, the terms may vary depending on the intention of a person of ordinary skill in the art, a judicial precedent, the appearance of a new technology, or the like. In addition, as a special case, there is a term that is arbitrarily selected by the applicant. When such a term is used, the meaning thereof will be in detail interpreted. Therefore, the meaning of the term used throughout the present specification should be defined in light of the present specification, instead of being interpreted as indicated by the name of the term.

Unless otherwise described, the expression "includes a constituent element," when used throughout the present specification, means "may further include any other constituent element, not "excluding any other constituent element." In addition, the term "unit," "module," or the like, which is used throughout the specification, means an individual physical entity that performs at least one function or operation and may be realized in hardware, software, or a combination of both. In addition, a constituent element, when referred to as being "connected to" one other constituent element, may be "directly connected to" one other constituent element or may be "indirectly connected to" one other constituent with an intervening constituent element in between.

An embodiment of the present invention will be described below in sufficient detail to enable a person of ordinary skill in the art to which the present invention pertains to practice the present invention without undue experimentation. However, the present invention may be practiced in various different forms and is not limited to the embodiment described below. For definite description of the embodiment of the present invention, a portion not associated therewith is omitted from the drawings, and the same constituent elements are given the same reference numeral throughout the present specification.

Figure 1:
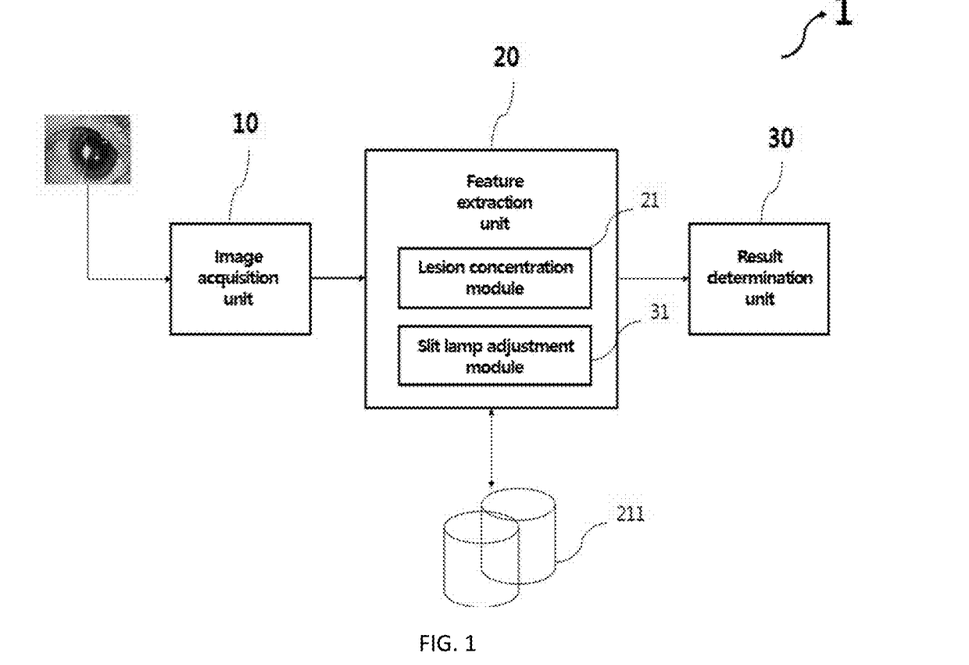
FIG. 1 is a block diagram illustrating a system for analyzing a corneal lesion using an anterior segment image according to the present invention.

FIG. 1 is a block diagram illustrating a system 1 for analyzing a corneal lesion using an anterior segment image according to the present invention.

With reference to FIG. 1, the system 1 according to the present invention includes an image acquisition unit 10, a feature extractor 20, and a result determination unit 30. The feature extractor 20 includes a lesion guiding module 21 that operates in conjunction with a slit lamp mask adjustment module 31 and a database, receives positional data 211 of a lesion, as an input, and learns a position of the lesion.

The image acquisition unit 10 may acquire the anterior segment image from an eyeball of the subject. The anterior segment image may be acquired through a slit lamp microscope in a doctor's office, a hospital, and the like or through the image acquisition unit 10 of a user's device or like. The user devices may include any devices, such as a smartphone, a tablet PC, and a digital camera, that include an imaging module and is capable of performing imaging.

The feature extractor 20 may extract feature information on the position and a cause of the lesion in the cornea from the anterior segment image by applying a convolution layer to the anterior segment image through machine learning on the basis of the database in which clinical information pre-acquired by analyzing positions and causes of lesions in the corneas of subjects is stored.

The result determination unit 30 may identify a position of the cornea from the anterior segment image using the feature information and may analyze and determine the position and the cause of the lesion in the cornea from the position of the cornea.

A machine learning model according to an embodiment of the present invention may include a deep neural network (DNN). The deep neural network refers to a neural network having a deep structure. The deep neural network is caused to learn a large amount of data to be learned in a structure made up of a multi-layered network and thus to automatically learn a feature of a signal and a relationship between signals. Accordingly, learning is performed on a network for diagnosing the anterior segment image.

Particularly, in order to determine a result of the diagnosis, a convolution neural network (CNN) may be used as a model for extracting the feature information from the anterior segment image.

Figure 2:
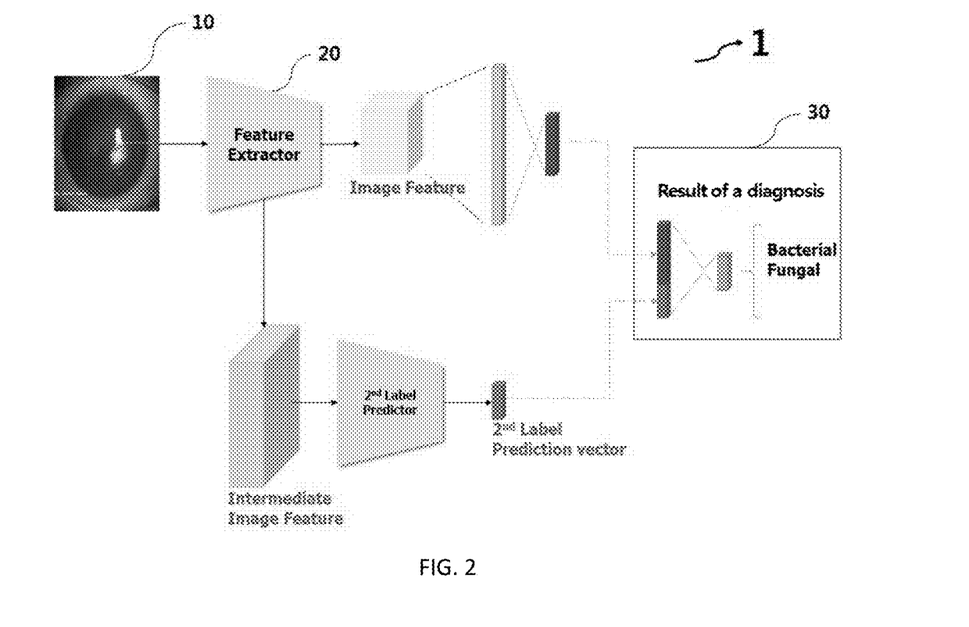
FIG. 2 is a schematic diagram illustrating that a result of a diagnosis is derived in the system for analyzing a corneal lesion using an anterior segment image according to the present invention.

FIG. 2 is a schematic diagram illustrating that the result of the diagnosis is derived in the system 1 for analyzing a corneal lesion using an anterior segment image according to the present invention.

With reference to FIG. 2, the result determination unit 30 may re-input a $3^{rd}$ label feature vector output from the feature extractor 20 and a prediction vector corresponding to a $2^{nd}$ label feature vector computed by applying a fully connected layer to the $3^{rd}$ label feature vector, into the fully connected layer and thus may identify the cause of the lesion in the cornea.

FIG. 2 is a diagram illustrating the entire system 1 for analyzing a corneal lesion, the system 1 utilizing the anterior segment image and a $2^{nd}$ label (a keyword set). When the anterior segment image is input into the feature extractor 20, $3^{rd}$ label vector feature information (image feature) is extracted. This feature information becomes a $2^{nd}$ label vector after passing through the fully connected layer.

The feature extractor 20 is configured to have the shape that results from stacking multiple convolutional layers on top of each other. Because of this, it is possible that an intermediate image feature is obtained between layers. The intermediate image feature is caused to pass through another deep learning network predicting a $2^{nd}$ label, and thus a $2^{nd}$ label prediction vector may be obtained.

A vector obtained from the above-described image feature and the $2^{nd}$ label prediction vector are added up, and the sum thereof is also caused to pass through the fully connected layer. Thus, a cause (bacterial or fungal) of keratitis that is a final result of the diagnosis may be obtained.

During a learning process in the entire system 1, a set of [an anterior segment image, result-of-diagnosis data, and $2^{nd}$ label data] is used, and when the set is actually used, only the anterior segment image is input.

Figure 3:
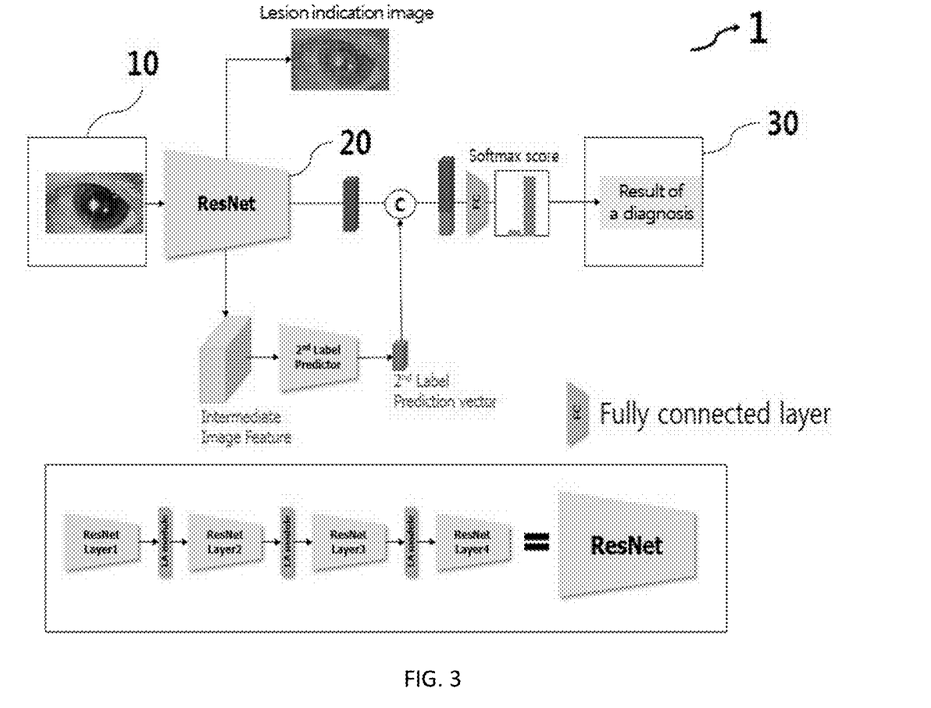
FIG. 3 is a diagram schematically illustrating the system for analyzing a corneal lesion using an anterior segment image according to the present invention.

FIG. 3 is a diagram schematically illustrating the system 1 for analyzing a corneal lesion using an anterior segment image according to the present invention.

With reference to FIG. 3, the feature extractor 20 may include a residual network (ResNet) obtained by stacking at least one network of a plurality of networks each including a convolution layer, a pooling layer, and an activation function or a rectified linear unit (ReLU) function, and the ResNet may extract the feature information, including a multiple-channel feature map for extracting a suspicious region, from the anterior segment image.

The lesion guiding module 21 is inserted between each of the ResNet layers. According to an embodiment of the present invention, the lesion guiding module 21 may go through a process four times. Regarding the feature extractor 20, a process for going through the ResNet layers four times in total may be expressed as the feature extractor 20. This process of processing data will be described below, together with a method of analyzing a corneal lesion.

According to an embodiment of the present invention, when the anterior segment image is input while in use, a lesion indication image may be obtained in the lesion guiding module (LG module) 21 inside the feature extractor 20. The $2^{nd}$ label vector and the $2^{nd}$ label prediction vector that pass through the feature extractor 20 and the fully connected layer may be concatenated.

Consequently, the result determination unit 30 may analyze and determine the position and the cause of the lesion in the cornea. This process may include a step of outputting, by the feature extractor 20, a $3^{rd}$ label feature vector, a step of outputting a prediction vector corresponding to a $2^{nd}$ label feature vector computed by applying a fully connected layer to the $3^{rd}$ label feature vector, and a step of re-inputting, by the result determination unit 30, the feature vector and the prediction vector into the fully connected layer.

The convolution neural network (CNN) is configured as illustrated n FIG. 3. According to an embodiment of the present invention, the feature extractor 20 may extract a feature of the anterior segment image, and, on the basis of the extracted feature, the result determination unit 30 may analyze and determine what causes a disease in the anterior segment image.

The feature extractor 20 may be configured with the convolution layer and the pooling layer (not illustrated), and a disease analysis unit 300 may be designed as the fully connected layer.

Specifically, in the convolution layer of the feature extractor 20, a feature map (not illustrated) may be formed by applying a plurality of filters in each region of the anterior segment image, and in the pooling layer (not illustrated), the feature map may be resized. In addition, the feature extractor 20 may be formed in such a manner that several convolution layer and several pooling layer are alternately arranged.

According to another embodiment of the present invention, instead of the fully connected layer (not illustrated), a classification model, such as a multiple-layer perception (MLP) or a support vector machine (SVM), may be included in the result determination unit 30. Thus, a prediction may be made through classification of the extracted features.

Figure 4:
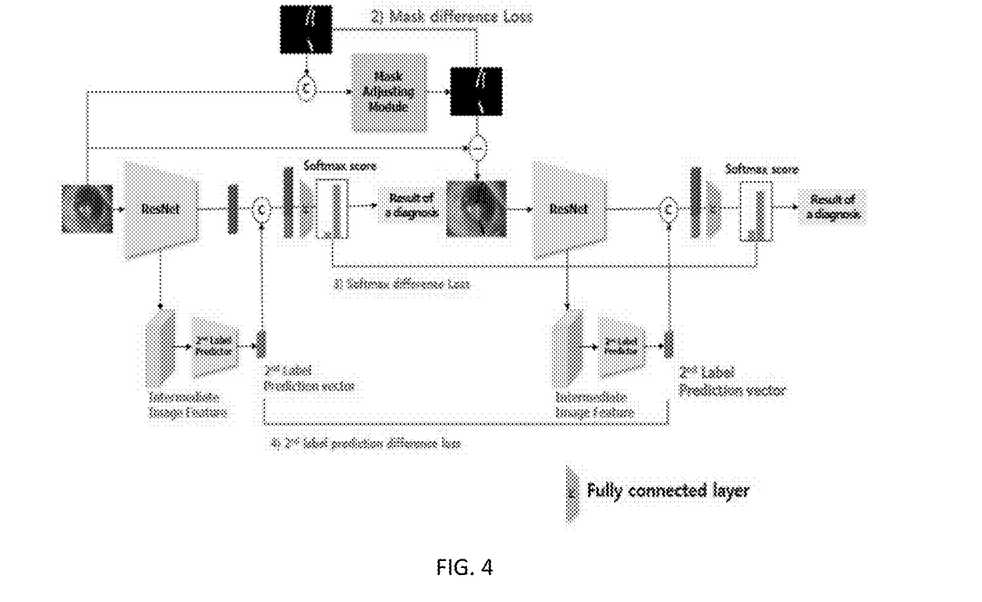
FIG. 4 is a diagram illustrating a learning process in the system for analyzing a corneal lesion according to an embodiment of the present invention.

FIG. 4 is a diagram illustrating the learning process in the system 1 for analyzing a corneal lesion according to an embodiment of the present invention. FIG. 4 is a diagram that results from combining the diagrams in FIGS. 2 to 4 to illustrate in detail the learning process in the system 1 for analyzing a corneal lesion according to the present invention.

With reference to FIG. 4, the anterior segment image and a result of a diagnosis by the slit beam mask in which a region of the anterior segment image on which the slit lamp sheds light is marked may be present as data used in the learning process. The data used in the learning process may be expressed as a set of [an anterior segment photograph, a slit beam mask, result-of-diagnosis correct answer (a cause of keratitis), and a $2^{nd}$ label correct answer]. At this point, only the anterior segment image may be used as an input in the system 1, and the other data are used to compute a loss function necessary in the leaning process.

The feature extractor 20 may include the lesion guiding module 21 and the slit lamp mask adjustment module 31. The lesion guiding module 21, as described above, may perform convolution of the positional data 211 of the lesion, which contains the position of the lesion in the cornea, and the $3^{rd}$ label feature vector and thus may compute the position of the lesion. The slit lamp mask adjustment module 31 may learn the anterior segment image, as clinical information, by adjusting a slit beam region present in a region of the anterior segment image.

Deep convolutional generative adversarial nets (DCGAN) may be used in order to accurately determine positional information of the lesion. However, according to an embodiment of the present invention, supervised learning based on the positional data 211 of the lesion that are marked by a medical specialist may be performed on the feature extractor 20.

The feature extractor 20 may include the ResNet and the lesion guiding module 21. During the learning process, the lesion guiding module 21 may serve to emphasize a feature map of a corresponding region in such a manner that the feature extractor 20 pays attention to the lesion.

At this point, the positional data 211 of the lesion (spatial attention ground truth (GT)) that are marked by the medical specialist are provided in such a manner as to serve as a correct answer for the supervised learning. The learning is performed in the direction of making a lesion segment extracted by the network consistent with the provided positional data 211 of the lesion.

The slit lamp mask adjustment module 31 may be caused to learn the position of the cornea or the position of the lesion in the cornea, which is included in the anterior segment image, with a slit lamp portion being excluded from the anterior segment image.

In addition, the slit lamp mask adjustment module 31 may adjust a masking region ratio by applying the convolution layer to the anterior segment image and the slit beam mask in which the region of the anterior segment image on which the slit lamp sheds light is marked. This masking processing process will be described below, together with the method of analyzing a corneal lesion.

The slit lamp mask adjustment module 31 is used only during the learning process in the system 1. An object of the slit lamp mask adjustment module 31 is to extract feature points of two different types of image input, that is, feature points of a broad beam and a slit beam.

The number of weighting factors used to perform the learning on the feature extractor 20 is limited, and because of this, a capacity for learning various feature points is also limited. Therefore, the more various types of images and the more various types feature points there are, the more difficult problem occurs. Thus, the accuracy can be reduced.

In the experimental example of the present invention, a case where a broad beam image and a slit beam image were learned separately from each other and a case where the broad beam image and the slit beam image were learned together were compared with each other. The result showed that, although more learning images were provided in the latter case than in the former case, there is seldom sufficient difference in accuracy between the former and latter cases.

In order to solve this problem, the slit lamp mask adjustment module 31 (used as a synonym for the slit lamp mask adjustment module) may prevent a slit beam portion that is expected to be extracted, as a feature point, by the system 1, but does not include the lesion, from being learned. Thus, the learning can be efficiently performed.

According to an embodiment of the present invention, color information of the lesion may include discoloration information of the cornea, the conjunctiva, or the sclera. For example, in a case where the cornea is infected, a color of the detected lesion can be expressed as white.

In addition, in the case of a staining photograph showing the infected cornea, anterior segment diseases may be classified through color information of the lesion, such as when a color of the detected lesion portion is expressed as green. Moreover, the anterior segment disease is determined, depending on a state of a blood vessel around the cornea. Therefore, blood-vessel information of a neighboring segment of the cornea may be feature information. Furthermore, like surface information of the conjunctiva or the sclera, the anterior segment disease can be classified according to surface roughness, surface smoothness, or the like. Moreover, the anterior segment diseases of eye may also be classified by each of the above-described pieces of feature information. However, among the above-described pieces of feature information, the anterior segment diseases of eye can be classified considering at least two pieces of feature information.

According to another embodiment of the present invention, the deep convolutional generative adversarial nets (DCGAN) may be included in the machine learning model of the feature extractor 20. The result determination unit 30 may output the position and the cause of the lesion, together with image information of the lesion that is extracted on the basis of the anterior segment image and the machine learning model.

Figure 5:
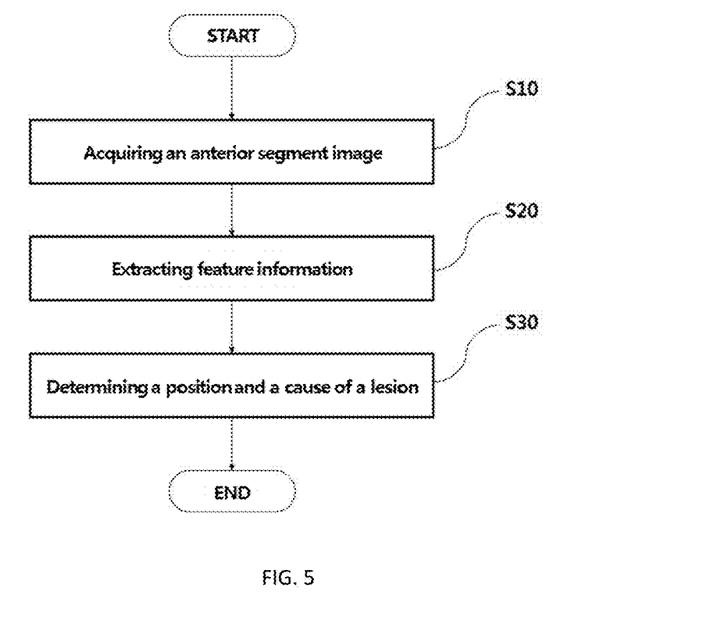
FIG. 5 is a flowchart illustrating the method of analyzing a corneal lesion using an anterior segment image according to the present invention.

FIG. 5 is a flowchart illustrating the method of analyzing a corneal lesion using an anterior segment image according to the present invention.

With reference to FIG. 5, the method of analyzing a corneal lesion according to the present invention may include Step S10 of acquiring an anterior segment image, Step S20 of extracting feature information, and Step S30 of determining a position and a cause of a lesion.

In Step S10 of acquiring an anterior segment image, the anterior segment image is acquired by the image acquisition unit 10 from the eyeball of the subject.

In Step S20 of extracting feature information, the feature extractor 20 extracts the feature information on the position and the cause of the lesion in the cornea from the anterior segment image by applying the convolution lay to the anterior segment image and the database in which the clinical information pre-acquired by analyzing the positions and causes of the lesions in the corneas of the subjects is stored.

In Step S30 of determining a position and a cause of a lesion, the result determination unit 30 identifies the position of the cornea in the anterior segment image using the feature information and analyzes and determines the position and the cause of the legion in the cornea.

Figure 6:
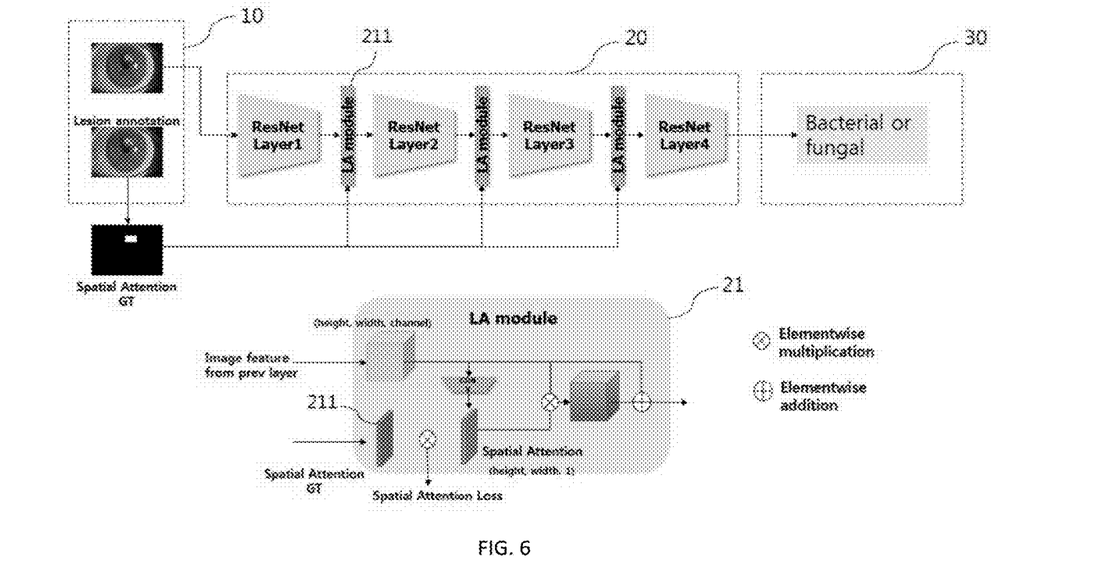
FIG. 6 is a block diagram illustrating a feature extractor and a lesion guiding module according to an embodiment of the present invention and processing that is performed by the feature extractor and the lesion guiding module.

FIG. 6 is a block diagram illustrating the feature extractor 20 and the lesion guiding module 21 according to an embodiment of the present invention and processing that is performed by the feature extractor 20 and the lesion guiding module 21.

With reference to FIG. 6, Step S20 of extracting feature information may include a step of extracting, the feature extractor 20, the feature information including a multiple-channel feature map in which a lesion region important for a diagnosis is emphasized, from the anterior segment image through the residual network (ResNet) having the plurality of layers and the lesion guiding module 21.

The ResNet has a network structure that is used universally in the field of deep learning, and the lesion guiding module 21 may be inserted between each of four layers of the ResNet. The lesion guiding module 21 uses the $3^{rd}$ label vector image feature, as an input, and this image feature represents an output value of each layer of the ResNet.

A label of the image feature is lowered while the image feature passes through the convolution layer inside the lesion guiding module 21 and thus, the image feature becomes a $2^{nd}$ label vector spatial attention. The spatial attention may function as a type of filter and may serve to increase a feature value of the important lesion segment by performing an element-wise multiplication arithmetic operation on the image feature.

The image feature in which the lesion segment is emphasized also goes through an operation of performing element-wide addition to an original image feature, and becomes an output of the lesion guiding module 21.

Step of extracting the feature information that is destined for the lesion guiding module 21 may include Step of performing convolution of the positional data 211 of the lesion that contains the position of the lesion in the cornea, and the $3^{rd}$ label feature vector.

According to an embodiment of the present invention, an output of the ResNet layer and the lesion guiding module 21 may also be used as an input of the ResNet layer. The feature that passes through all four layers of the ResNet that serve as the feature extractor 20 may pass through the fully connected layer in which the result determination unit 30 finally performs disease analysis. Then, a result of a final diagnosis as keratitis may be output.

During the learning process, the positional data 211 of the lesion (spatial attention GT) that are marked by the medical specialist may be input into the lesion guiding module 21. The learning may be performed on the lesion guiding module 21 in the direction of ensuring consistency with the positional data 211 of the lesion (spatial attention is spatial attention GT) and accurately predicting the result of the diagnosis.

Figure 7:
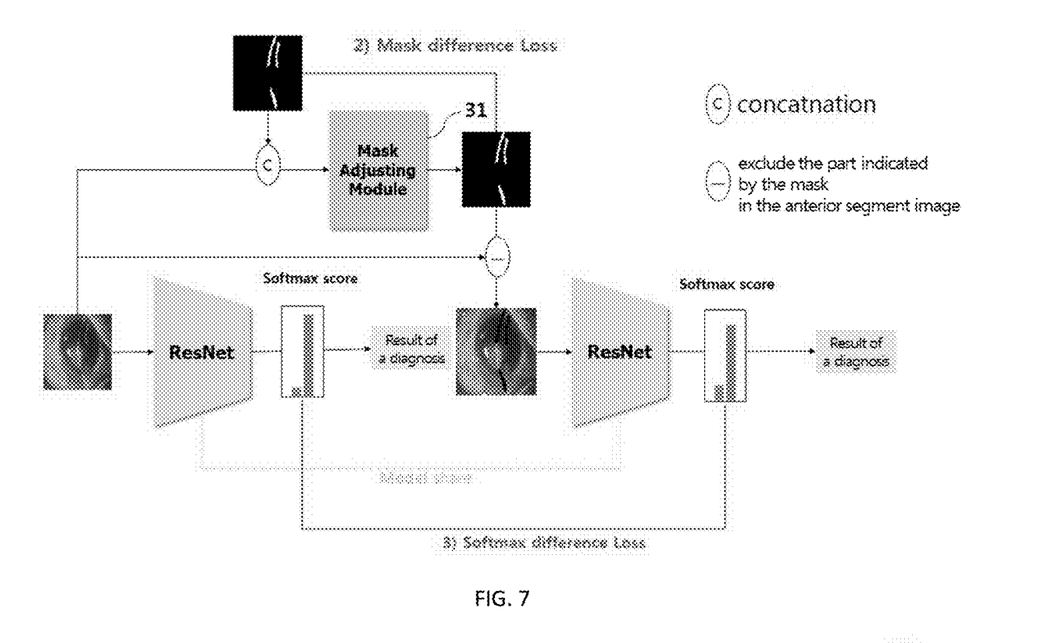
FIG. 7 is a block diagram illustrating the feature extractor and a slit lamp mask adjustment module according to an embodiment of the present invention and processing that is performed by the feature extractor and the slit lamp mask adjustment module.

FIG. 7 is a block diagram illustrating the feature extractor 20 and the slit lamp mask adjustment module 31 according to an embodiment of the present invention and processing that is performed by the feature extractor 20 and the slit lamp mask adjustment module 31.

With reference to FIG. 7, the method may proceed to Step of adjusting, by the slit lamp mask adjustment module 31 of the feature extractor 20, the slit beam image present in the region of the anterior segment image The slit lamp mask adjustment module 31 (mask adjusting module) is a module that is used only for the learning process in the system 1 for analyzing a corneal lesion. The slit lamp mask adjustment module 31 operates in such a manner that leaning image data in which the broad beam image and the slit beam image are both present are efficiently learned.

An input of the slit lamp mask adjustment module 31 is a mask photograph showing a position of the slit lamp in the anterior segment image. An output thereof is a photograph in the form of a mask, but varies slightly from a first input mask photograph in terms of contents.

The learning process may be performed in the direction of reducing three loss functions.

1) Cross entropy loss is a loss function that is used universally in deep learning. The more accurate the result of the diagnosis, the more decreased a value thereof.
2) Mask difference loss is a loss function that sets a mask passing through the slit lamp mask adjustment module 31 and an input mask in such a manner as not to vary widely from each other. The more similar the input mask and an output mask are to each other, the more decreased a value thereof.
3) Softmax difference loss is a loss function that represents a difference between the results of the diagnosis. During the learning process, one slit beam image passes two times through the system 1 for analyzing a corneal lesion. At this point, the first time the slit beam image passes, an original photograph may be used, and the second time the slit beam image passes, the anterior segment image whose portion marked by the mask passing through the slit lamp mask adjustment module 31 is excluded may be used.

The image feature passing through the ResNet changes into a vector with a size of 2×1 while passing through the fully connected layer in which the result determination unit 30 performs the disease analysis.

Values of the vectors are referred to as softmax scores, and may be computed as a score indicating whether the input anterior segment image represents bacterial or fungal keratitis.

As a softmax score output from a photograph in which the slit lamp portion is hidden and a softmax score output from the original photograph become more similar to each other, the slit lamp portion results in having less influence on the result of the diagnosis. Using the softmax difference loss principle, the learning may be performed on the network in the direction of not considering the slit lamp portion as being important.

As the softmax score output from the photograph in which the slit lamp portion is hidden and the softmax score output from the original photograph becomes more similar to each other, the value of the loss function is more decreased.

Figure 8:
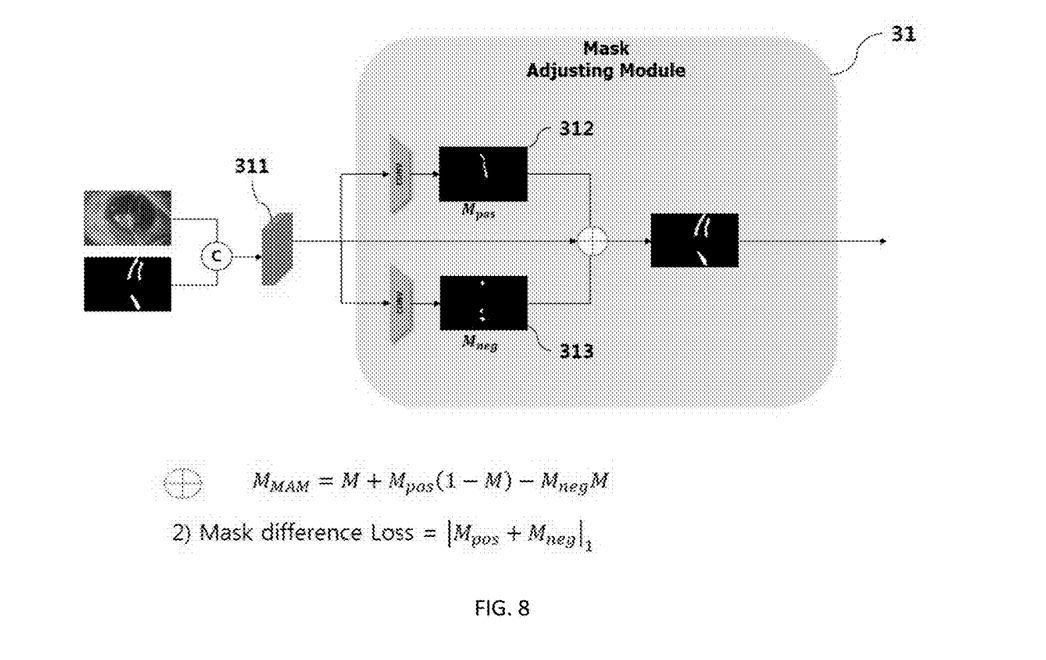
FIG. 8 is a diagram illustrating a process in which according to an embodiment of the present invention, the slit lamp mask adjustment module adjusts an original mask by applying a weighting factor to an original mask.

FIG. 8 is a diagram illustrating a process in which according to an embodiment of the present invention, the slit lamp mask adjustment module 31 adjusts an original mask 311 by applying a weighting factor to the original mask 311.

With reference to FIG. 8 illustrating the inside of the slit lamp mask adjustment module 31, the process may include Step of applying, by the slit lamp mask adjustment module 31, a convolution layer to an anterior segment image and a pre-collected slit lamp region mask and Step of adjusting a masking region ratio by applying the convolution layer to the anterior segment image and a slit beam mask in which a region of the anterior segment image on which the slit lamp sheds light is marked.

The anterior segment image and a mask representing a slit beam portion of a corresponding image are concatenated, and a result of the concatenating is an input of the slit lamp mask adjustment module 31, and a $3^{rd}$ label vector being input passes through the convolution layer and becomes an M_pos mask 312 and an M_neg mask 313 that are referred to as masks indicating how much the original mask 311 is adjusted.

That is, a portion of the original mask 311 that is represented by the M_neg mask 313 disappears, and a portion thereof that is represented by the M_pos mask 312 appears. A finally adjusted mask may be an output of the slit lamp mask adjustment module 31.

The symbol ⊕ indicating that the M_pos mask 312 and the M_neg mask 313 in FIG. 8 are concatenated refers to computation for adjusting the original mask 311 using the M_pos mask 312 and the M_neg mask 313. As described above, the more decreased a difference between a final mask and the original mask 311, the more decreased the mask difference loss has to be. Because of this, the mask difference loss can be expressed as the sum of weighting factors of the M_pos mask 312 and the M_neg mask 313 (the mask always has a positive value).

The pre-acquired clinical information to be applied to the learning process according to an embodiment of the present invention will be described below. The experimental example of the embodiment of the present invention shows the anterior segment image, the positional data 211 of the lesion, and the result of the diagnosis that are reflected in the learning process by the feature extractor 20.

FIGS. 9 to 12 are photographs showing a process of generating the clinical information according to the present invention. A process of accumulating the above-described database after being analyzed by a doctor or a medical specialist is shown.

Figure 9:
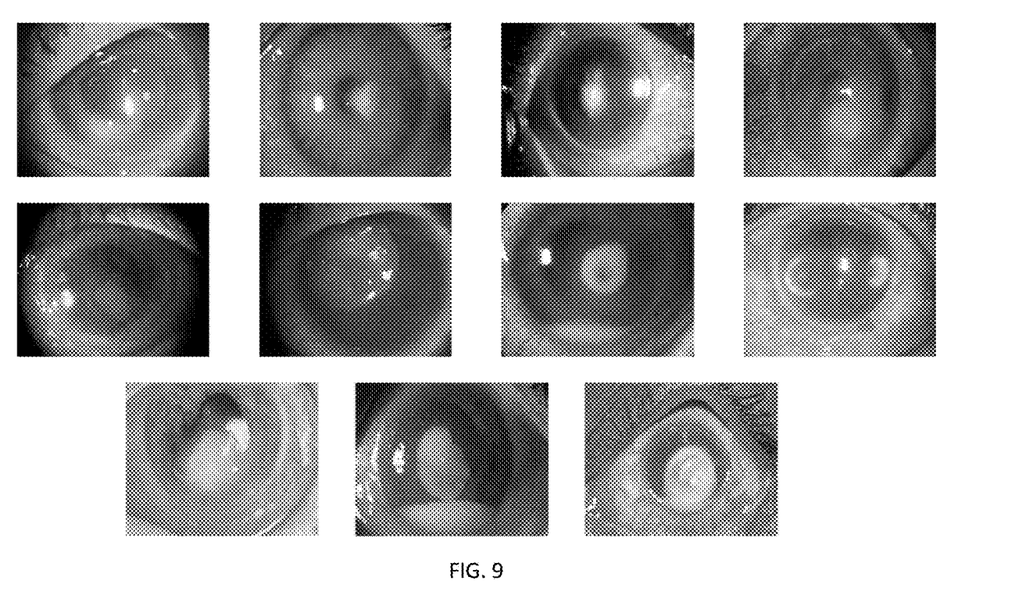
FIG. 9 is photographs for clinical information reference on bacterial keratitis among anterior segment images according to an embodiment of the present invention.
Figure 10:
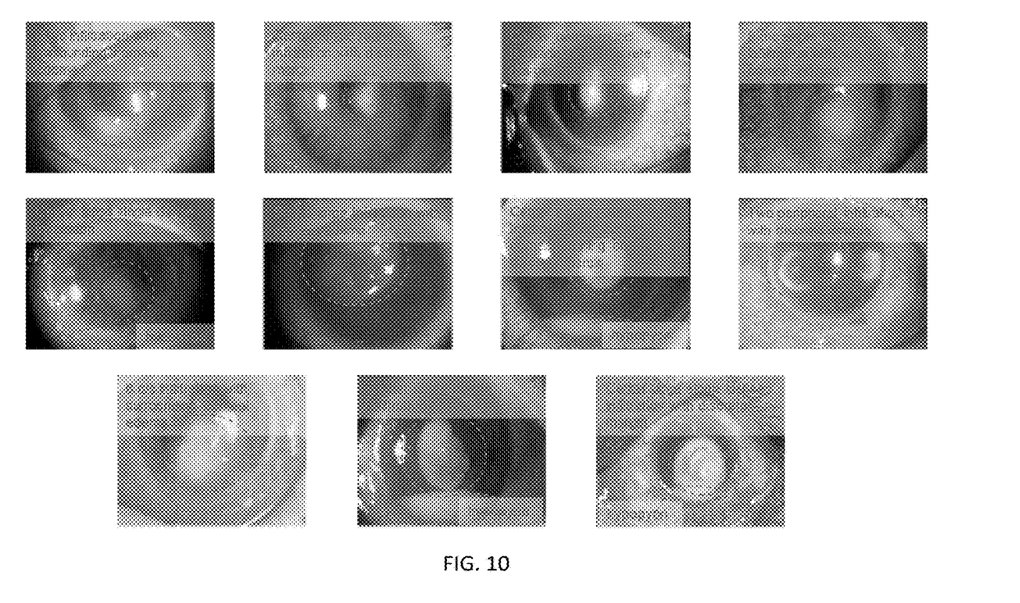
FIG. 10 is photographs showing the clinical information resulting from a medical specialist analyzing positions and causes of lesions in the anterior segment image in FIG. 8 in order to build a database in which the clinical information is stored.
Figure 11:
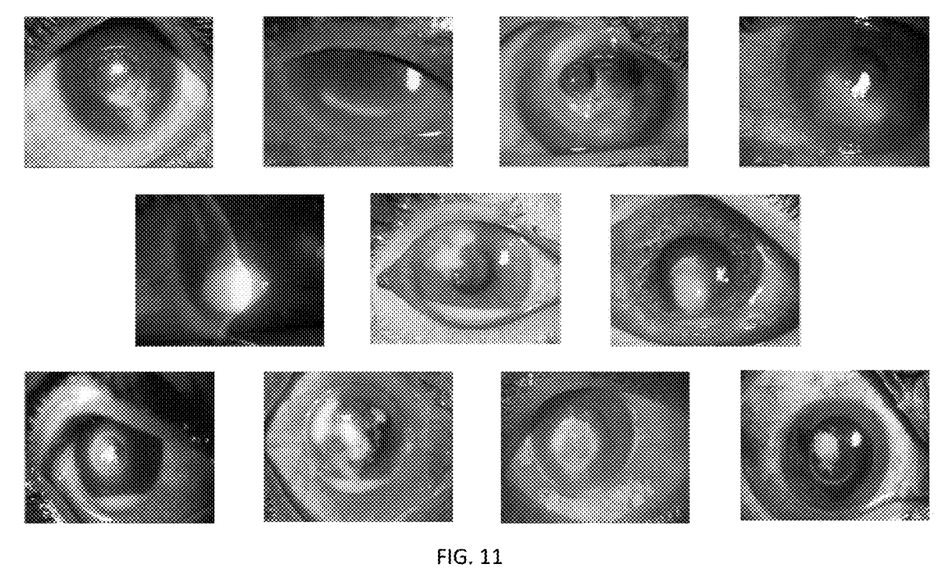
FIG. 11 is photographs showing a fungal keratitis in the anterior segment image according to an embodiment of the present invention.
Figure 12:
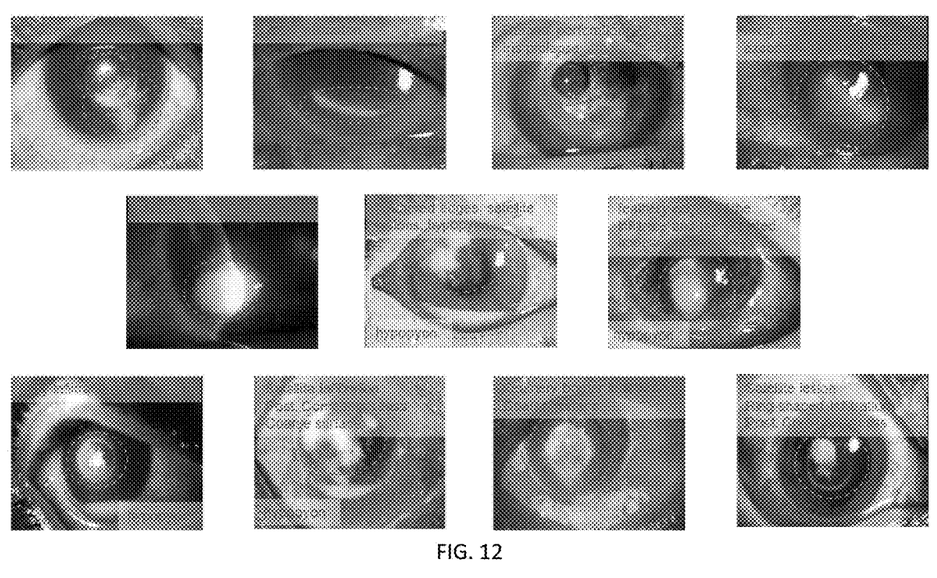
FIG. 12 is photographs showing the clinical information resulting from the medical specialist analyzing the positions and the causes of the lesions in the anterior segment image in FIG. 10 to build the database in which the clinical information is stored.

FIGS. 9 and 11 are clinical-information reference photographs for bacterial keratitis (FIG. 9) and fungal keratitis (FIG. 11) in the anterior segment image according to an embodiment of the present invention. FIGS. 10 and 12 are photographs showing the clinical information resulting from the medial specialist analyzing the positions and the causes of the lesions in FIGS. 9 and 11 in order to build the database.

That is, FIGS. 10 and 12 are photographs showing results of image labeling performed by three medical specialists. A process in which a distinctive lesion segment in each of the off-line generated results of the diagnosis is marked and in which an appearance of the legion is marked is shown.

According to an embodiment of the present invention, anterior segment diseases of eye may be classified by a structure of the anterior segment and a type of disease. Regarding the structure of the anterior segment of eye, the anterior segment may include the cornea, the conjunctiva, the sclera, the anterior chamber, the lens, the iris, the ciliary body, and the like.

In addition, the anterior segment diseases of eye may include all infectious inflammatory diseases associated with bacteria, viruses, and fungi, non-infectious inflammatory diseases, such as an autoimmune disease, non-inflammatory diseases, such as degeneration, dystrophy, and keratoconus, and diseases associated with the anterior segment of eye, such as dry eye disease, cataract, corneal erosion, deposit, edema, and corneal opacity.

That is, types of anterior segment diseases of eye may be classified into infectious and non-infectious inflammatory diseases due to the structure of the anterior segment, and anterior segment diseases due to non-inflammation, trauma, aging, and the like.

Figure 13:
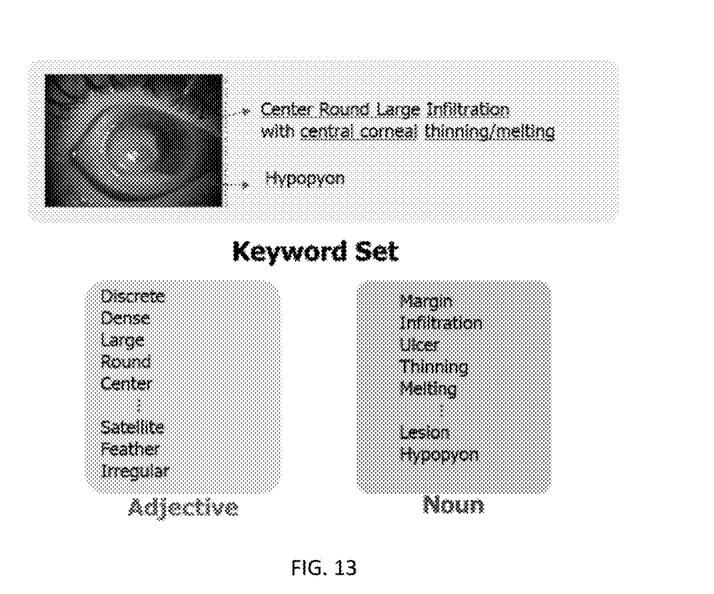
FIG. 13 is a diagram illustrating that contents obtained by analyzing the clinical information in the anterior segment image in FIGS. 9 to 12 are produced as a keyword set.
Figure 14:
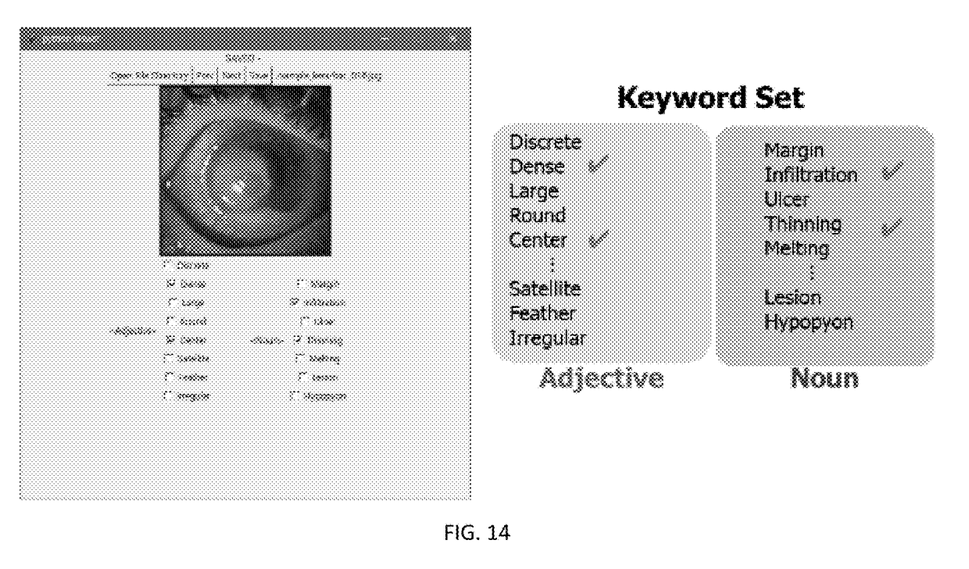
FIG. 14 is a view illustrating a screen on which the keyword set in FIG. 13 is displayed for outputting when a program runs according to an embodiment of the present invention.

FIG. 13 is a diagram illustrating that contents obtained by analyzing the clinical information in the anterior segment image in FIGS. 9 to 12 are produced as a keyword set. FIG. 14 is a view illustrating a screen on which the keyword set is displayed for outputting when a program runs.

The present invention may be practiced as a computer-readable storage device on which a program for realizing the method of analyzing a corneal lesion is recorded and may be realized as a program. In a case where the anterior segment image is input, the position and the cause of the lesion in the cornea can be identified with the method according to the present invention that uses machine learning.

Instructions for each lesion that are written by the medical specialist are attached to the anterior segment image, and adjectives and nous that are frequently used in the instructions can be extracted and produced as the keyword set. With reference to the medical specialist-written instructions for the lesion, labelling with the keyword corresponding to each anterior segment image may be performed.

According to another embodiment of the present invention, medical information may be included. The medical information may include at least one of current-state information of the anterior segment of eye, future-state prediction information of the anterior segment of eye, and treatment information for a disease class.

In addition, the current-state information of the anterior segment of eye may be information in which a type of disease of the anterior segment and a disease class thereof are included together. The future-state prediction information of the anterior segment of eye may be predicted through the machine learning model. For this prediction, the machine learning model may additionally include a recurrent neural network (RNN) and a multi-layer perceptron (MLP), and the like.

The future-state prediction information may include a type of disease that is predicted to occur according to a current state of the anterior segment of eye, and the degree to which the disease develops, and may also include expected rejection in accordance with the current state. Treatment information for the disease class may include an anterior segment disease of eye resulting from the classification and the treatment information in accordance with the disease class.

As described above, according to the present invention, a patient can be diagnosed with keratitis on the basis of the accurate diagnosis model built on the basis of a large amount of existing data, instead of being diagnosed depending on an ophthalmologist's personal clinical knowledge and experience. Thus, a misdiagnosis rate can be greatly lowered, and thus prognosis of the patient's eyesight can also be improved.

Susceptibility of a causative organism of keratitis to an antibiotic tends to change with time. However, the continually updated database that is to be applied according to the present invention may be quickly adapted to this change, and thus a suitable diagnosis consistent with a current trend can be provided.

In addition, the system for and the method of analyzing a corneal lesion according to the present invention may be distributed to an area where a few licensed medical facilities are located and where an ophthalmologist does not do his/her medical practice, thereby contributing to an increase in equal access to domestic medical service. Moreover, the system and method can greatly contribute to decreasing unnecessary medical expenses incurred due to an erroneous diagnosis or treatment of a patient with keratitis. Thus, the saved money can be used to provide medical treatments to patients suffering from other principal diseases. The distribution of the system and the method to a developing country can contribute to an international community development and a world health improvement.

The exemplary embodiments of the present inventions are in detail described above, and it would be understandable to a person of ordinary skill in the art to which the present invention pertains that various modifications to the embodiments described above are possibly made without departing from the scope of the present invention. Therefore, the scope of the present invention should be defined not only by the following claims, but also by all alterations and modifications that are derived from the concept of equivalents of the claims, without being defined in a manner that is limited to the embodiments described above.

The invention claimed is:

1. A system for analyzing a corneal lesion using an anterior segment image, the system comprising:
    an image acquisition unit configured to acquire the anterior segment image from an eyeball of a subject;
    a feature extractor configured to extract feature information on a position and a cause of a lesion in a cornea of the eyeball from the anterior segment image by applying a convolution layer to the anterior segment image through machine learning on the basis of a database in which clinical information pre-acquired by analyzing positions and causes of lesions in the corneas of subjects is stored; and
    a result determination unit configured to identify a position of the cornea from the anterior segment image using the feature information and to analyze and determine the position and the cause of the lesion in the cornea from the position of the cornea;
    wherein the feature extractor comprises a slit lamp mask adjustment module adjusting a slit beam image present in a region of the anterior segment image,
    wherein the slit lamp mask adjustment module applies the convolution layer to the anterior segment image and an already-collected slit lamp region mask and then adjusts a masking ratio by applying a weighting factor for a slit beam portion.

2. The system of claim 1, wherein the feature extractor comprises:
    a residual network (ResNet) obtained by stacking at least one network of a plurality of networks each including a convolution layer, a pooling layer, and an activation function or a rectified linear unit (ReLU) function and the ResNet extracts the feature information, including a multiple-channel feature map for extracting a suspicious region, from the anterior segment image.

3. The system of claim 2, wherein the feature extractor comprises:
    a lesion guiding module configured to extract a lesion region more precise than the suspicious region through convolution of the feature information and positional data of a lesion in the clinical information, the positional data representing a position of the lesion.

4. The system of claim 1, wherein the slit lamp mask adjustment module excludes a slit lamp portion from the anterior segment image and causes the position of the cornea or the position of the lesion in the cornea, which is included in the anterior segment image, to be learned.

5. The system of claim 1, wherein the result determination unit re-inputs a $3^{rd}$ label feature vector output from the feature extractor and a prediction vector corresponding to a $2^{nd}$ label feature vector computed by applying a fully connected layer to the $3^{rd}$ label feature vector, into the fully connected layer and thus identifies the cause of the lesion in the cornea.

6. A method of analyzing a corneal lesion using an anterior segment image, the method comprising:
    a step of acquiring, by an image acquisition unit, the anterior segment image from an eyeball of a subject;

a step of extracting, by a feature extractor, feature information on a position and a cause of a lesion in a cornea of the eyeball from the anterior segment image by applying a convolution layer to the anterior segment image and a database in which clinical information pre-acquired by analyzing positions and causes of lesions in the corneas of subjects is stored; and a step of analyzing and determining, by a result determination unit, the position and the cause of the lesion in the cornea after identifying a position of the cornea from the anterior segment image using the feature information;

wherein the step of extracting, by the feature extractor, the feature information comprises, a step of adjusting, by a slit lamp mask adjustment module of the feature extractor, a slit beam image present in a region of the anterior segment image; and wherein the step of adjusting, by the slit lamp mask adjustment module, the slit beam image comprises a step of applying, the slit lamp mask adjustment module, the convolution layer to the anterior segment image and an already-collected slit lamp region mask and a step of adjusting a masking ratio by applying a weighting factor for a slit beam portion.

7. The method of claim 6, wherein the step of extracting, by the feature extractor, the feature information comprises:

a step of extracting the feature information including a multiple-channel feature map for extracting a suspicious region, from the anterior segment image, the feature information being destined for a residual network (ResNet) obtained by stacking at least one network of a plurality of networks each including a convolution layer, a pooling layer, and an activation function or a rectified linear unit (ReLU) function.

8. The method of claim 7, wherein the step of extracting the feature information comprises:

a step of extracting a lesion region more precise than the suspicious region through convolution of the feature information and positional data of a lesion in the clinical information, the positional data representing a position of the lesion, by a lesion attention module.

9. The method of claim 6, wherein the step of determining, by the result determination unit, the position and the cause of the lesion in the cornea comprises:

a step of outputting, by the feature extractor, a $3^{rd}$ label feature vector;

a step of outputting a prediction vector corresponding to a $2^{nd}$ label feature vector computed by applying a fully connected layer to the $3^{rd}$ label feature vector; and a step of re-inputting, by the result determination unit, the feature vector and the prediction vector to the fully connected layer.

10. A non-transitory computer-readable storage device on which a program that performs a method of analyzing a corneal lesion using an anterior segment image is recorded, the method comprising:

a step of acquiring, by an image acquisition unit, the anterior segment image from an eyeball of a subject;

a step of extracting, by a feature extractor, feature information on a position and a cause of a lesion in a cornea of the eyeball from the anterior segment image by applying a convolution layer to the anterior segment image and a database in which clinical information pre-acquired by analyzing positions and causes of lesions in the corneas of subjects is stored; and a step of analyzing and determining, by a result determination unit, the position and the cause of the lesion in the cornea after identifying a position of the cornea from the anterior segment image using the feature information;

wherein the step of extracting, by the feature extractor, the feature information comprises, a step of adjusting, by a slit lamp mask adjustment module of the feature extractor, a slit beam image present in a region of the anterior segment image; and wherein the step of adjusting, by the slit lamp mask adjustment module, the slit beam image comprises a step of applying, the slit lamp mask adjustment module, the convolution layer to the anterior segment image and an already-collected slit lamp region mask and a step of adjusting a masking ratio by applying a weighting factor for a slit beam portion.

\* \* \* \* \*